US012629661B2

(12) United States Patent
Salgaonkar et al.

(10) Patent No.: US 12,629,661 B2
(45) Date of Patent: May 19, 2026

(54) PHOTO CATALYTIC DEVICE FOR CONTINUOUS PROCESS FOR CO-CONVERSION OF CO₂+H₂O TO C1-OXYGENATES IN SUNLIGHT

(71) Applicant: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), Delhi (IN)

(72) Inventors: Kranti Nishikant Salgaonkar, Pune Maharashtra (IN); Chinnakonda Subramanian Gopinath, Pune Maharashtra (IN)

(73) Assignee: COUNCIL OF SCIENTIFIC AND INDUSTRIAL RESEARCH AN INDIAN REGISTERED BODY INCORPORATED UNDER THE REGN. OF SOC. ACT (ACT XXI OF 1860), New Delhi (IN)

( * ) Notice: Subject to any disclaimer, the term of this patent is extended or adjusted under 35 U.S.C. 154(b) by 608 days.

(21) Appl. No.: 18/042,864

(22) PCT Filed: Aug. 24, 2021

(86) PCT No.: PCT/IN2021/050814
§ 371 (c)(1),
(2) Date: Feb. 24, 2023

(87) PCT Pub. No.: WO2022/044039
PCT Pub. Date: Mar. 3, 2022

(65) Prior Publication Data
US 2023/0330632 A1 Oct. 19, 2023

(30) Foreign Application Priority Data
Aug. 24, 2020 (IN) ............................. 202011036464

(51) Int. Cl.
| | |
|---|---|
| *C07C 45/67* | (2006.01) |
| *B01D 53/00* | (2006.01) |
| *B01D 53/86* | (2006.01) |
| *B01D 53/88* | (2006.01) |
| *B01J 21/06* | (2006.01) |
| *B01J 23/22* | (2006.01) |
| *B01J 23/42* | (2006.01) |
| *B01J 23/44* | (2006.01) |
| *B01J 23/755* | (2006.01) |
| *B01J 27/04* | (2006.01) |
| *B01J 35/33* | (2024.01) |
| *B01J 35/39* | (2024.01) |
(Continued)

(52) U.S. Cl.
CPC .......... *B01J 21/063* (2013.01); *B01D 53/007* (2013.01); *B01D 53/8671* (2013.01); *B01D 53/885* (2013.01); *B01J 23/22* (2013.01); *B01J 23/42* (2013.01); *B01J 23/44* (2013.01); *B01J 23/755* (2013.01); *B01J 27/04* (2013.01); *B01J 35/33* (2024.01); *B01J 35/39* (2024.01); *B01J 35/45* (2024.01); *C07C 29/156* (2013.01); *C07C 29/157* (2013.01); *C07C 45/65* (2013.01); *B01D 2255/1021* (2013.01); *B01D 2255/1023* (2013.01); *B01D 2255/20707* (2013.01); *B01D 2255/20738* (2013.01); *B01D 2255/20753* (2013.01); *B01D 2255/20761* (2013.01); *B01D 2255/802* (2013.01); *B01D 2257/504* (2013.01); *B01J 2235/05* (2024.01); *B01J 2235/30* (2024.01)

(58) Field of Classification Search
CPC . B01J 21/063; B01J 35/45; B01J 35/39; B01J 35/33; B01J 23/22; B01J 23/142; B01D 53/007; B01D 53/885; C07C 45/65; C07C 29/157
See application file for complete search history.

(56) References Cited

U.S. PATENT DOCUMENTS

2019/0381476 A1 12/2019 Grimes et al.

FOREIGN PATENT DOCUMENTS

WO WO-2022044039 A1 3/2022

OTHER PUBLICATIONS

"International Application No. PCT/IN2021/050814, International Search Report and Written Opinion mailed Dec. 2, 2021", (Dec. 2, 2021), 10 pgs.
(Continued)

*Primary Examiner* — Sikarl A Witherspoon
(74) *Attorney, Agent, or Firm* — Schwegman Lundberg & Woessner, P.A.

(57) ABSTRACT

The present invention discloses a dual functional photocatalytic device and a process for photocatalytic co-conversion of CO₂ and H₂O to value added products in direct sunlight. More particularly, the present invention relates to efficient and continuous process for the photocatalytic co-conversion of a mixture of CO₂ and water into methanol, formaldehyde, in the presence of newly developed dual-functional photocatalyst device. The present invention is to provide dual-functional photocatalyst device, along with a co-catalyst and integrating them into a photocatalytic device using artificial leaf approach wherein said device is in the form of thin film working under wide spectrum of solar radiation at ambient conditions. Additionally it is easy to scale up the photocatalyst device size from 1 cm² to 10 cm² size and process is tuneable to generate desired products.

19 Claims, 5 Drawing Sheets

(51) Int. Cl.

| | |
|---|---|
| *B01J 35/45* | (2024.01) |
| *C07C 29/156* | (2006.01) |
| *C07C 29/157* | (2006.01) |
| *C07C 45/65* | (2006.01) |

(56) References Cited

OTHER PUBLICATIONS

Kim, Chansol, et al., "Z-scheme Photocatalytic CO2 Conversion on Three-Dimensional BiVO4/Carbon-Coated Cu2O Nanowire Arrays under Visible Light", ACS Catal. 2018, 8, 5, 4170-4177. (Apr. 5, 2018), 4170-4177.

Ran, Jingrun, et al., "Cocatalysts in Semiconductor-based Photocatalytic CO2 Reduction: Achievements, Challenges, and Opportunities", Advanced Materials, vol. 30, Issue 7, 2018; https://doi.org/10.1002/adma.201704649, (Jan. 8, 2018), 118 pgs.

Wu, Yimin A., et al., "Facet-dependent active sites of a single Cu2O particle photocatalyst for CO2 reduction to methanol", Nat Energy 4, 957-968 (2019) //https://doi.org/10.1038/s41560-019-0490-3, (Nov. 4, 2019), 957-968.

Xu, Luyi, et al., "Research Progress in Conversion of CO2 to Valuable Fuels", Molecules 2020, 25, 3653; doi:10.3390/molecules25163653, (Aug. 11, 2020), 23 pgs.

Kim, Chansol, et al., "Z-scheme Photocatalytic CO2 Conversion on Three-Dimensional BiVO4/Carbon-Coated Cu2O Nanowire Arrays under Visible Light", ACS Catal. 2018, 8, 4170-4177, (Apr. 5, 2018), 4170-4177.

Ran, Jingrun, et al., "Cocatalysts in Semiconductor-based Photocatalytic CO2 Reduction: Achievements, Challenges, and Opportunities", Adv. Mater. 2018, 30, 1704649, (2018), 31 pgs.

CH₂(OH)₂

CH₃OH

PHOTO CATALYTIC DEVICE FOR CONTINUOUS PROCESS FOR CO-CONVERSION OF $CO_2+H_2O$ TO C1-OXYGENATES IN SUNLIGHT

PRIORITY CLAIM TO RELATED APPLICATIONS

This application is a U.S. national stage filing under 35 U.S.C. § 371 from International Application No. PCT/IN2021/050814, filed on 24 Aug. 2021, and published as WO2022/044039 on 3 Mar. 2022, which claims the benefit under 35 U.S.C. 119 to India Application No. 202011036464, filed on 24 Aug. 2020, the benefit of priority of each of which is claimed herein, and which applications and publication are hereby incorporated herein by reference in their entirety.

FIELD OF THE INVENTION

The present invention relates to a dual functional photocatalytic device for continuous process for the photocatalytic co-conversion of $CO_2$ and water into value added products under direct sunlight. Particularly, the present invention relates to a process for the co-conversion of $CO_2$ and water into value added products such as methanol, formaldehyde, by using the newly developed dual-functional photocatalyst along with a co-catalyst and integrating them into a photocatalytic device using artificial leaf approach.

BACKGROUND AND PRIOR ART OF THE INVENTION

The quest for sustainable fuel/energy/chemicals production to meet the demands of a constantly rising global population is one of the main challenges for mankind in this century. Worldwide concern over the impact of green-house gas emissions, particularly $CO_2$ emission, on climate change are increasingly evident from the increasing number of disasters, such as severe drought, very heavy rain, due to continuous deployment of fossil fuels for all energy/fuel needs in the last one century. It is an urgent need to reduce our dependency on fossil-fuel based energy. $CO_2$ utilization as a chemical feedstock is an attractive and necessary strategy to ameliorate carbon emissions while offering sustainable, safe and economical methods to convert $CO_2$ into value added chemicals. Harvesting abundant sunlight in solving environmental problems is a promising approach and one of the ultimate goals for the sustainability of global development; hence the photocatalytic conversion of $CO_2$ with solar energy is the most appealing route for $CO_2$ conversion to generate value-added and renewable fuels/chemicals.

Several efforts have been made till date by scientists to achieve this conversion. The article entitled *"Facet-dependent active sites of as single $Cu_2O$ particle photocatalyst for $CO_2$ reduction to methanol"* by Yimin A. Wu et al. and published in the journal *Nature Energy, Vol* 4, November 2019, 957-968 reports the highest $CO_2$ reduction, till date, to methanol, at the rate of 1.2 mol/h·g of the catalyst with solar to fuel efficiency of 10%. In this case, $Cu_2O$ nanoparticles are used in powder form suspended in water and the reaction is evaluated at 0.01 g. $Cu_2O$ dispersed in water is continuously flushed with $CO_2/H_2O$ gas mixture till the solution is saturated with $CO_2$. $CO_2$ saturated $Cu_2O$ containing solution is illuminated with a 300 W Xe lamp between 0 and 60 min. under continuous $CO_2/H_2O$ flow and the product is analyzed periodically. This paper reports adsorption effect is the dominant effect of photocatalytic $CO_2$ reduction on (110) facets of single $Cu_2O$ particle into methanol; however, (100) facet of $Cu_2O$ is inert. However, the results are demonstrated at 0.01 g (10 mg) particulate catalyst weight, which produces 0.133 mmol/s of methanol and yet to be demonstrated at higher scale, although it is claimed to produce 1.2 mol/h·g methanol. In fact, 0.133 mmol/s and 1.2 mol/h·g do not match by extrapolation from s to h by a factor of 3600 (1 h=3600 s). It is to be noted that, unlike conventional catalysis, there are many difficulties/issues associated with scaling up the photocatalysis experiments with larger amount of photocatalysts and indeed lower activity is reported at higher scale (eg. 1 g level) of catalysts.

It is very well known in the literature that activity obtained with small amount of particulate photocatalyst (typically 1-100 mg) does not linearly increase with increasing amount of catalyst (say 1 g and higher), rather it decreases.

There is also a need in the art to provide a process, which is also scalable to larger size photoanodes to harvest solar energy for the above chemical conversion at a commercially affordable level.

OBJECTIVES OF THE INVENTION

The main objective of the present invention is to provide a dual functional photocatalytic device for continuous process for the photocatalytic co-conversion of $CO_2$ and water into value added products under direct sunlight.

Another objective of the present invention is to provide an efficient and continuous process for the photocatalytic co-conversion of a mixture of $CO_2$ and water in the presence of newly developed dual-functional photocatalyst [photoanode] device.

Yet another objective of the present invention is to provide dual-functional photocatalyst device, wherein said device is in the form of thin film working under wide spectrum of solar radiation at ambient conditions.

Yet another objective of the present invention is to scale up the photocatalyst device from 1 $cm^2$ to 10 $cm^2$ size and demonstrate its feasibility for continuous process.

SUMMARY OF THE INVENTION

Accordingly, present invention provides a dual functional photocatalytic device comprising:
  i. a Visible-light absorbing semiconductor [VAS] assembled in the pore of a wide band gap semiconductor and;
  ii. integrated with a co catalyst in thin film form;
  wherein
  Visible-light absorbing semiconductor [VAS] is selected from the group comprising of earth abundant 3d or 4d transition metals, metal oxides alone or in combinations thereof;
  wide gap semiconductor is selected from $TiO_2$ or ZnO;
  Co-catalyst is selected from the group comprising of earth abundant 3d or 4d transition metals, metal oxides alone or in combination thereof.

In an embodiment of the present invention, said Visible-light absorbing semiconductor [VAS] used is selected from the group comprising of $BiVO_4$, CdS and PbS.

In yet another embodiment of the present invention, said Visible-light absorbing semiconductor [VAS] is in the mesopores of the wide band gap semiconductor in the form of quantum dots (QDs).

In another embodiment of the present invention, said co-catalyst is selected from the group consisting of nano pallidum (Pd), Platinum (Pt), Gold (Au), Silver (Ag), Nickel (Ni), Cobalt (Co), Cuprous oxide ($Cu_2O$), NiCu alloy, Ti, Si or Zn, Nickel oxide, manganese oxide, Iron oxides, NiFe, $0.5\theta_{Pt}$@NiFe, $0.5\theta$Pt@NiCu, $0.5\theta_{Pt}$@Pd, NiFe alloy or Pt-coated NiCu alloy.

In yet another embodiment of the present invention, said device shows stable activity for 50 h while maintaining product yield and selectivity.

In yet another embodiment, present invention provides a fabrication process of the photoanode device comprises assembling visible light absorbing semiconductor from their ionic components and depositing directly inside the pores of the wide band gap semiconductor.

In yet another embodiment, present invention provides a process for the photocatalytic co-conversion of a mixture of $CO_2$ and water to value added products in batch mode comprising the step of:

i. injecting $CO_2$ into a water to maximum saturation level and placing a photocatalytic device in a quartz reactor under light source at a temperature in the range of 1 to 60° C.;

wherein said light source used selected from UV+Visible light, visible light and direct sunlight.

In yet another embodiment, present invention provides a process for the photocatalytic co-conversion of a mixture of $CO_2$ and water to value added products in continuous mode comprising the step of:

i. continuously flowing $CO_2$ through water with photocatalytic device in a quartz reactor under light source at a temperature in the range of 1-60° C.;

wherein said light source used is selected from UV+Visible light, visible light and direct sunlight.

In yet another embodiment of the present invention, value added product is selected from methanol and formaldehyde.

In yet another embodiment of the present invention, conversion efficiency of said carbon dioxide to value added products is in the range of 35-55%.

In yet another embodiment of the present invention, said process is tunable to generate desired value-added products selected from methanol and formaldehyde.

DETAILED DESCRIPTION OF THE INVENTION

Figure 1:
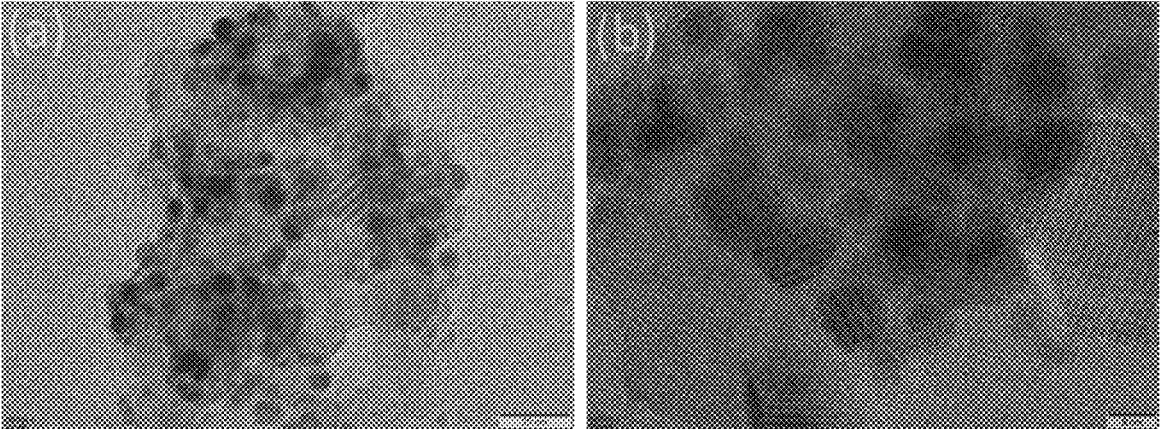
FIG. 1 represents TEM images of photoanode material exhibiting Bismuth vanadate [$BiVO_4$] QDs in the mesopores of titania and heterojunctions formed between $BiVO_4$ and $TiO_2$ $BiVO_4$ QDs are observed to be in a size range of 3-5.5 nm and dark contrast characterizes them. Bigger titania particles can be seen with light/grey contrast. Scale bar is 20 and 5 nm in panel (a) and (b), respectively.
Figure 2:
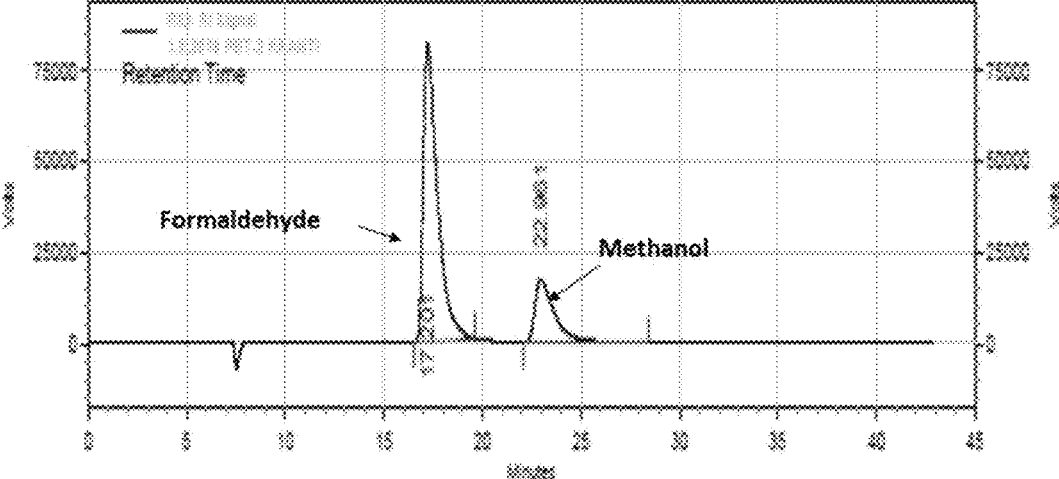
FIG. 2 represents HPLC results obtained for the product analysis for the co-conversion of water and $CO_2$ in the presence of photocatalyst device made of Pd—$BiVO_4$/$TiO_2$ film and direct sunlight, after 5 h of irradiation.
Figure 3:
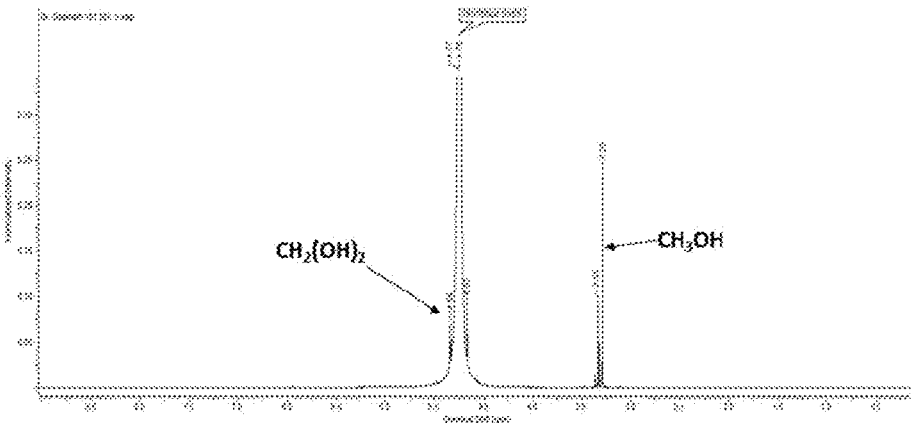
FIG. 3 represents NMR spectra recorded with the products obtained after the co-conversion of water and $CO_2$ in the presence of photocatalyst device made of the Pd—$BiVO_4$/$TiO_2$ film. Note the similarity in products obtained in NMR and HPLC analysis in FIG. 2.
Figure 4:
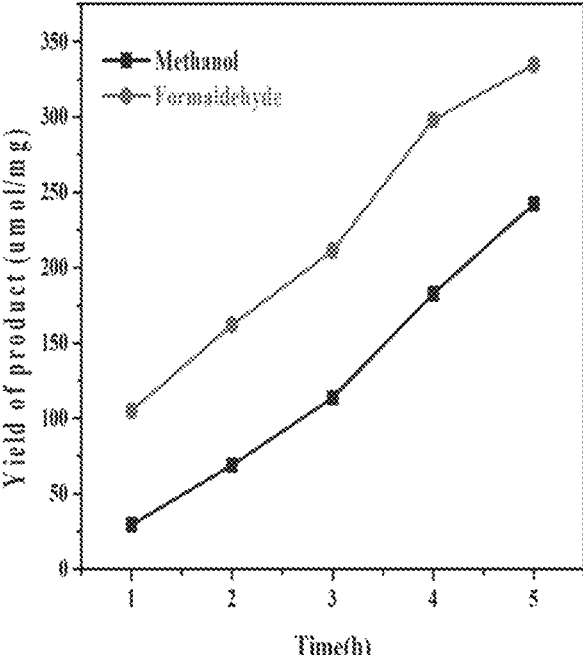
FIG. 4 represents products yield obtained as a function of irradiation time for the co-conversion of water and $CO_2$ in the presence of photocatalyst device made of the Pd—$BiVO_4$/$TiO_2$.
Figure 5:
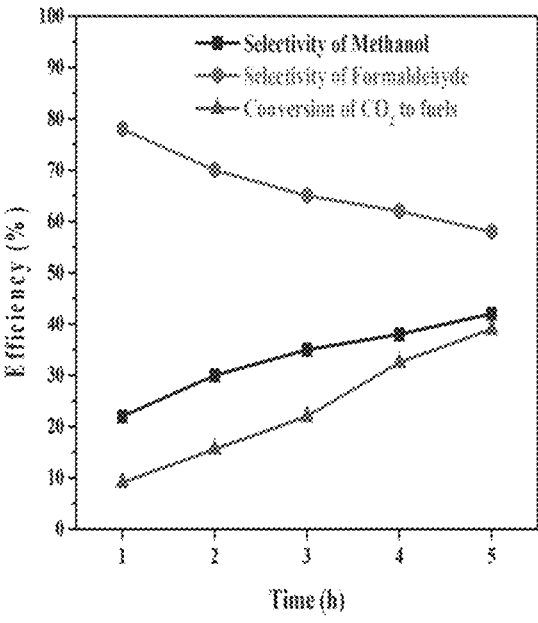
FIG. 5 represents conversion of $CO_2$ and selectivity of the products obtained as a function of irradiation time for the co-conversion of water and $CO_2$ in the presence of photocatalyst device made of the Pd—$BiVO_4$/$TiO_2$.

Present invention provides a dual-functional photocatalyst device, wherein said photocatalyst comprises of two or more semiconductors by creating heterojunction between them, more particularly it consists of quantum dots (QDs) of suitable semiconductor in the pores of wide band gap semiconductors, such as $TiO_2$ or ZnO.

Present Invention Provides a Dual Functional Photoanode Device Comprising:

i. visible-light absorbing semiconductor (VAS) in wide gap semiconductor;

ii. a co-catalyst in thin film form; wherein wide gap semiconductor is selected from $TiO_2$ or ZnO;

VAS is selected from the group comprising of earth abundant 3d or 4d transition metals, metal oxides alone or in combinations thereof;

The VAS used is selected from the group comprising of $BiVO_4$, CdS and PbS.

The VAS used is preferably $BiVO_4$ in the pores of $TiO_2$ as a quantum dots of 3-5.5 nm in size.

Co-catalyst is selected from the group comprising of earth abundant 3d or 4d transition metals, metal oxides alone or in combination thereof.

Further the co-catalyst is selected from the group consisting of palladium (Pd), Platinum (Pt), Gold (Au), Silver (Ag), Nickel (Ni), Cobalt (Co), Cuprous oxide ($Cu_2O$), NiCu alloy, Ti, Si or Zn, Nickel oxide, manganese oxide and Iron oxides. NiFe, $0.5\theta_{Pt}$@NiFe, $0.5\theta$Pt@NiCu, $0.5\theta_{Pt}$@Pd.

Preferably Pd nanocubes and NiCu alloy are used as a co-catalyst.

The VAS is in the mesopores of the wide gap semiconductor [$TiO_2$] in the form of quantum dots (QDs).

Co-catalyst is selected from the group consisting of nano palladium, NiCu alloy, NiFe alloy, Pt-coated NiCu alloy.

The photocatalyst comprises of $BiVO_4$/$TiO_2$ and Pd as a co-catalyst. $BiVO_4$ QD and $TiO_2$ act as active visible and UV light absorbing photocatalyst components respectively.

The present invention provides a process for the photocatalytic co-conversion of a mixture of $CO_2$ and water into the value added products in direct sunlight or simulated sunlight in the presence of newly developed dual-functional photocatalyst and a co-catalyst in the device form.

Thus, the present invention provides a process for the photocatalytic production of liquid and/or gaseous chemicals and/or fuels, such as methanol, formic acid, formaldehyde, two carbon containing products (like ethanol), by irradiating a mixture of $CO_2$ and water in the presence of a photocatalyst in the form of thin film device, wherein said device works under wide spectrum of solar radiation. Optionally it works in UV, visible and/or UV+visible light sources also.

The process for the photocatalytic co-conversion of a mixture of $CO_2$ and water comprises of injecting the carbon dioxide $CO_2$ into the water and photocatalyst device placed in a quartz reactor under solar light illumination or a suitable light source at a temperature in the range of 1-60° C. $CO_2$ was dissolved in water to the maximum saturation levels.

Lower temperature increases the $CO_2$ solubility and enhances the reaction rate towards higher yield in a single batch. $CO_2$ saturated aqueous solution was illuminated with sunlight in the presence of the photocatalyst device to afford the value added products, which were analyzed periodically by HPLC analytical method. Optionally, product analysis can be made with NMR method also. In many cases, HPLC and NMR methods were used parallelly for quantitative measurements.

The process for the photocatalytic co-conversion of mixture of $CO_2$ and water may be carried out in a batch process or in a continuous process. To convert the batch process, as described above, into a continuous process, the co-conversion of $CO_2$ and water is carried out under the continuous flow of $CO_2$ in direct sunlight in a three-neck quartz reactor for $CO_2$ circulation and collecting the products. Products formed in the gas phase are condensed and collected outside the reactor in a cold trap and analyzed for its content by GC and HPLC. Products that remain in the solution were also analyzed by HPLC and/or NMR methods. Product(s) concentration measured from cold trap and from the solution is added to get the total amount of product(s) and selectivity.

The fabrication process of the solar light responsive photocatalyst device comprises of assembling light absorbing quantum dots from their ionic components and depositing directly inside and outside the pores of $TiO_2$ or ZnO thin film.

A uniform thickness in the range of 8-12 micron thick titania film was prepared by standard Doctor Blade method. Thus, prepared $TiO_2$ or ZnO thin films were integrated with quantum dots into its pores by Successive Ionic Layer Adsorption and Reaction (SILAR) method. To introduce $BiVO_4$ into the pores of titania thin film, prepared by doctor blade method, was subjected to SILAR method with $Bi^{3+}$ and vanadyl species containing solutions in a particular sequence. SILAR helps to assemble of $BiVO_4$ QDs of particle size 3-5.5 nm uniformly in the mesopores of $TiO_2$ or ZnO and distribution over the entire thickness of the film. This helps to create heterostructure formation between $BiVO_4$ and $TiO_2$ due to the employment of SILAR method for the assembly of the former in the latter. The heterostructure of $BiVO_4$ and $TiO_2$ all over the film helps in effective separation of electron-hole pair as well as dispersion of electrons toward the co-crystal hence towards better activity of photocatalyst.

The support for thin films is selected from the group comprising of any conductive or semiconducting surfaces including glass plate, glass vessels/glass containers, indium tin oxide (ITO) glass plate, fluorine-doped tin oxide (FTO) glass plate, silicon wafer, stainless steel preferably FTO, ITO, silicon wafer, stainless steel plates.

Conversion efficiency of carbon dioxide to value added chemicals is in the range of 35-55% and solar to fuel efficiency (STF) calculated to be ~11.2% by adopting the equation of: STF=Energy of methanol produced/solar energy irradiated on the device.

Within this disclosure, direct sunlight was employed without using any filter. However, simulated sunlight with standard light source and filters, UV+Visible, Visible, UV light sources are also optionally used.

Within this disclosure "wide band-gap semiconductors" means any semiconductor material with a band gap of 2-4 eV and having conduction band energy more negative than reduction potential of $CO_2$ to any possible reduction products, such as HCHO, $CH_3OH$, CO, HCOOH, $CH_4$, but not limited to the above. Wide gap semiconductors include, but are not limited to, $TiO_2$ or ZnO.

The present invention provides a process for photo catalyst co conversion of water and $CO_2$, said process comprises carrying out a flow of $CO_2$ with photocatalyst device in a reactor in the presence of direct sunlight to afford the products.

The present invention provides a process for the photocatalytic production of liquid and/or gaseous chemicals and/or fuels, such as methanol, formic acid, formaldehyde, two carbon containing products (like ethanol), by irradiating mixture of $CO_2$ and water in the presence of a photocatalyst in the form of thin film device, wherein said device works under wider spectrum of solar radiation. Optionally it works in UV+visible light sources also.

The present invention provides the process for the photocatalytic co-conversion of a mixture of $CO_2$ and water to value added products in direct sunlight comprising the steps of:

a) injecting gas-phase carbon dioxide $CO_2$ into water and placing a photocatalyst device in a quartz reactor under solar light illumination or a suitable light source at a temperature in the range of 1-60° C.;

b) dissolving the carbon dioxide $CO_2$ in water to the maximum saturation levels;

c) illuminated the $CO_2$ saturated aqueous solution with sunlight in the presence of the photocatalyst device to afford the value added products;

d) analyzing the value added products by HPLC analytical method and/or NMR method.

The value added products are selected from methanol or formaldehyde.

Lower temperature increases the $CO_2$ solubility and enhances the reaction rate towards higher yield in a single batch.

The process for the photocatalytic co-conversion of mixture of $CO_2$ and water may be carried out in a batch process or in a continuous process.

To convert the batch process, as described above, into a continuous process, the co-conversion of $CO_2$ and water is carried out under the continuous flow of $CO_2$ in direct sunlight in a three-neck quartz reactor for $CO_2$ circulation and collecting the products. Products formed in the gas phase are condensed and collected outside the reactor in a cold trap and analyzed for its content by GC and HPLC. Products that remain in the solution was also analyzed by HPLC and/or NMR methods. Product(s) concentration measured from cold trap and from the solution is added to get the total amount of product(s) and selectivity.

A process provides $CO_2$ reduction, wherein a modified $TiO_2$ device i.e. doctor blade method prepared mesoporous titania thin film with quantum dots assembled in the pores of titania and integrated with a co-catalyst, is irradiated with direct sunlight in the presence of $CO_2$ and $H_2O_2O$ to form methanol and formaldehyde.

Benefits of this method are, direct conversion of solar energy using wireless photochemical device into value added chemicals.

Titania thin film with quantum dots of $BiVO_4$ assembled in the pores have band gap ~2.4 eV absorbing visible light so almost 47% solar spectrum falling on earth is consumed. Method is easy to apply without any sophisticated device just by using $CO_2$ and water.

In yet another embodiment, the device size can be scaled up to large sizes to maximize solar light absorption and subsequent production of large amount of value added chemicals, such as methanol, formaldehyde.

Conversion efficiency of carbon dioxide to value added chemicals by this process is in the range of 35-55% to an amount of carbon dioxide and solar to fuel efficiency ~11.2%.

Another embodiment of the present invention provides a dual-functional photocatalyst device, wherein said photo-catalyst comprises of two or more semiconductors by creating heterojunction between them, more particularly it consists of quantum dots (QDs) of suitable semiconductor in the pores of wide band gap semiconductors, such as $TiO_2$ or ZnO. In a particularly useful embodiment, the photocatalyst comprises of $BiVO_4/TiO_2$ and Pd as a co-catalyst with $BiVO_4$ QD and $TiO_2$ as the active visible and UV light absorbing photocatalyst components, respectively.

The fabrication process of the solar light responsive photocatalyst device comprises of assembling light absorbing quantum dots from their ionic components and depositing directly inside the pores of $TiO_2$ or ZnO thin film.

A uniform thickness in the range of 8-12 micron thick titania film was prepared by standard Doctor Blade method. Thus, prepared $TiO_2$ or ZnO thin films were integrated with quantum dots into its pores by Successive Ionic Layer Adsorption and Reaction (SILAR) method.

To introduce $BiVO_4$ into the pores of titania thin film, prepared by doctor blade method, was subjected to SILAR method with $Bi^{3+}$ and vanadyl or metavanadate species containing solutions in a particular sequence.

Ionic precursors assembled in the mesopores lead to $BiVO_4$ formation within the pores upon calcination at 450° C. Critically, SILAR helps to assemble the precursors of $BiVO_4$ in the mesopores of $TiO_2$ and assist in the formation of $BiVO_4$QDs of particle size 3-5.5 nm uniformly and distributed over the entire thickness of the film. This helps to create heterostructure formation between $BiVO_4$ and $TiO_2$ due to the employment of SILAR method for the assembly of the former in the latter. The heterostructure of $BiVO_4$ and $TiO_2$ all over the film helps in effective separation of electron-hole pair as well as dispersion of electrons toward the co-catalyst hence towards better activity of photocatalyst. Importantly, this is the first time it is demonstrated that an oxide material is assembled from its precursors (or ionic components) into another oxide material. Definite pore size or pore size range associated with titania does not allow $BiVO_4$ particle to grow bigger than the pore diameter and hence a precise particle size control is made available. TEM image shown in FIG. 1 fully supports the presence of $BiVO_4$ exclusively within the pores of titania, and demonstrating a junction observed between $BiVO_4$ and titania.

SILAR helps to assemble of $BiVO_4$ QDs of particle size 3-5.5 nm uniformly in the mesopores of $TiO_2$ and distribution over the entire thickness of the film. High resolution images shows that $BiVO_4$ QDs are spherical in shape with particle size in the range of 3 to 5.5 nm. (FIG. 1) Distinct heterostructure formation (FIG. 1b) was observed between $BiVO_4$ and $TiO_2$ due to the employment of SILAR method for the assembly of QDs in mesoporous $TiO_2$. Mesoporous $TiO_2$ film made by doctor blade method, allows the diffusion of ionic components of $Bi^{3+}$ and $VO_3^-$ and thus $BiVO_4$ QDs forms in the pores of $TiO_2$ upon calcination. The heterostructure of $BiVO_4$ and $TiO_2$ observed all over the film helps in better electron-hole separation as well as dispersion of electrons towards co-crystal.

The support for thin films is selected from the group comprising of any conductive or semiconducting surfaces including glass plate, glass vessels/glass containers, indium tin oxide (ITO) glass plate, fluorine-doped tin oxide (FTO) glass plate, silicon wafer, stainless steel. In particular useful embodiment, substrate was chosen for thin films is FTO, ITO, silicon wafer, stainless steel plates.

Integration of wide band gap semiconductor with light absorbing semiconductors in the form of quantum dots is one of the promising method, as quantum dots exhibit high surface area, possess tunable band gaps and band edge positions because of quantum confinement, and have shorter charge transfer pathways helps to provide more potential energy for photochemical reaction. Quantum dots of $BiVO_4$, CdS, PbS can be used for integrating wide gap semiconductors. Semiconductors with mesoporous structure are recognized to be efficient to improve the photocatalytic activity towards $CO_2$ reduction due to high surface area and enhanced adsorption of $CO_2$.

VAS-QDs is selected from the group comprising of $BiVO_4$, CdS, and PbS. In particularly useful embodiment, the VAS used is $BiVO_4$ in the pores of $TiO_2$.

Total thickness of the film is maintained in the range of ~8-15 μm and it is confirmed from thickness measurements by profilometer and SEM analysis. It is worth to note that no separate layer of deposited components are observed rather only single uniform and smooth layer of thin film on FTO is seen. Hence it suggests porous network of $TiO_2$ allows diffusion of $Bi^{3+}$ and $VO_3^-$ and thus $BiVO_4$ forms in the pores of $TiO_2$ upon calcination. Selectivity of the products can be tuned by reaction time as well as by employing different co-catalyst.

Under the experimental condition, 1 mg of $BiVO_4/TiO_2$ (of which 97.5±0.5 wt % is titania and 2.0-2.5 wt % is $BiVO_4$ QDs) is coated as thin film over 1 $cm^2$ area and integrated with Pd-co-catalyst as a device. This device is kept in 30 ml of deionized water (pH=7) in a 50 ml quartz reactor at room temperature (28±3° C.). The reaction mixture is thoroughly degassed initially using 99.9% $CO_2$ gas for 10 min at 25-30° C. to remove any dissolved oxygen. Subsequently, the reaction mixture is kept in an ice bath (1-3° C.) and continuously purged with $CO_2$ for additional 30 min to obtain the saturated solution of $CO_2$ in water. Total amount of $CO_2$ dissolved in the water is measured to be 1.48 mmol, which is measured through simple titration with NaOH solution (0.01 M). A possible reaction sequence that might occur under the experimental conditions is given below:

$$2CO_2+2H_2O \rightarrow 2HCHO+2O_2$$

$$2HCHO+2H_2O \rightarrow 2CH_3OH+O_2$$

Total is $$2CO_2+4H_2O \rightarrow 2CH_3OH+3O_2$$

Hence, by simply carrying out the reaction for longer hours would lead to high selectivity of methanol, while formaldehyde is produced selectively at shorter time. It is observed that methanol yield is in the range of 30-50 μmol/h·mg·$cm^2$ (1 mg catalyst ($BiVO_4$+$TiO_2$) coated over 1 $cm^2$ area) and formaldehyde yield is 100-130 μmol/h·mg·$cm^2$ and the maximum conversion efficiency of carbon dioxide to value added chemicals is in range of 35-55%. And selectivity of methanol and formaldehyde is approximately 30% and 70% respectively. The lower and higher range of the yield shown above for both products is with the standard one sun conditions in the laboratory and direct sunlight, respectively. When the experiments are carried out in direct sunlight up to 35% higher conversion of $CO_2$ and higher range of products yield are observed. This is due to the light flux from sunlight and also depends on the time of the day it is irradiated. In addition, direct sunlight exposure increases the temperature between 45-60° C., depending on the time of the day and solar flux conditions. Significantly high temperature available, due to the above conditions, increases the rate of the reaction, which is an added advantage in doing the reaction in direct sunlight. Generally, higher activity is observed between 11 am and 3 pm and activity decreases before and after the above time window.

TABLE 1

CO$_2$ conversion and products selectivity and yield as a function of irradiation time with BiVO$_4$/TiO$_2$ 1 cm$^2$ size photoanode integrated with Pd co-catalyst in batch process under one sun condition.

| Time, h | CH$_3$OH Yield μmol/mg | Selectivity | HCHO Yield μmol/mg | Selectivity | CO$_2$ Conversion to fuel % |
|---|---|---|---|---|---|
| 1 | 29.4 | 22% | 105 | 78% | 9.1% |
| 2 | 69 | 30% | 162 | 70% | 15.6% |
| 3 | 113.7 | 35% | 211.2 | 65% | 22% |
| 4 | 182.7 | 38% | 298.2 | 62% | 32.5% |
| 5 | 242.4 | 42% | 334.5 | 58% | 39% |

Experimental results shown in Table 2 was carried out with similar conditions, but with large device of 10 cm$^2$ (4 cm×2.5 cm). The results obtained are shown in Table 2, which is in good agreement with table 1 and suggesting a linear increase in activity with device size.

TABLE 2

CO$_2$ conversion and products selectivity and yield as a function of irradiation time with BiVO$_4$/TiO$_2$ 10 cm$^2$ photoanode integrated with Pd co-catalyst in batch process under one sun condition.

| Time, h | CH$_3$OH Yield μmol/mg | Selectivity | HCHO Yield μmol/mg | Selectivity | CO$_2$ Conversion to fuel % |
|---|---|---|---|---|---|
| 1 | 302 | 22% | 1020 | 78% | 9.0% |
| 3 | 1127 | 35% | 2120 | 65% | 22.2% |
| 5 | 2455 | 42% | 3350 | 58% | 39.1% |

Photocatalysis experiments were also carried out with 1 cm$^2$ photoanode device coated only with titania, and without any BiVO$_4$ QDs in it to measure the activity contribution from titania. Same experimental conditions were maintained as that of the results shown in Table 1. Neither significant conversion of $CO_2$ nor any products formation were observed, even after 5 hours of continuous irradiation under one sun conditions. This underscores the predominant role of BiVO$_4$ QDs in converting solar light into value added chemicals. Ten times higher value of products yield observed with 10 cm$^2$ device (Table 2) (compared to 1 cm$^2$ device, results shown in Table 1), due to ten times larger amount of BiVO$_4$ QDs underscores the increase in activity is linear with device size and the QD content. In view of this direct correlation the photocatalytic activity of the device size that would contain 1 mg of BiVO$_4$ QDs is shown in Table 3.

TABLE 3

Products yield with 1 mg of BiVO$_4$ QDs assembled in the large area BiVO$_4$/TiO$_2$photoanode device

| Time, h | CH$_3$OH Yield mmol/mg of BiVO$_4$ | Selectivity | HCHO Yield mmol/mg of BiVO$_4$ | Selectivity |
|---|---|---|---|---|
| 1 | 1.5 | 22% | 5.2 | 78% |
| 2 | 3.4 | 30% | 8.1 | 70% |
| 3 | 5.7 | 35% | 10.6 | 65% |
| 4 | 9.1 | 38% | 14.9 | 62% |
| 5 | 12.1 | 42% | 16.7 | 58% |

Simple and linear multiplication of the values given in Table 3 leads to MeOH and HCHO production rate of 2.42 and 3.34 mol/g·h for a gram of BiVO$_4$ QDs. This is again based on the average rate obtained at the end of 5 h of reaction time. As both are single carbon containing products (like $CO_2$), it is assumed the total product concentration to be 5.76 mol/g·h with the assumption that both products are equal. In fact equivalent amount of $CO_2$ (5.76 moles of $CO_2$ corresponds to 253.4 g) gets converted in to value added products in 5 h of reaction time. Hence the solar to fuel conversion efficiency was calculated with methanol using solar simulator having one sun condition with the above photocatalyst system. The incident illumination power density is 100 mW/cm$^2$ and irradiation area is 100 cm$^2$. Possible chemical reaction is $CO_2 + 2H_2O \rightarrow CH_3OH + \frac{3}{2}O_2$. Gibbs free energy of this reaction is 702.2 kJ/mol.

Solar to fuel efficiency is 11.2%, which is calculated as follows:

$$= \{(CH_3OH \text{ yield} * \Delta G)/(P_{total} * \text{Area})\}$$

$$\{(1.6 \text{ mmol/s} \times 702 \text{ kJ/mol})/(100 \text{ mW/cm}^2 \times 100 \text{ cm}^2)\} = 11.2\%$$

Figure 8:
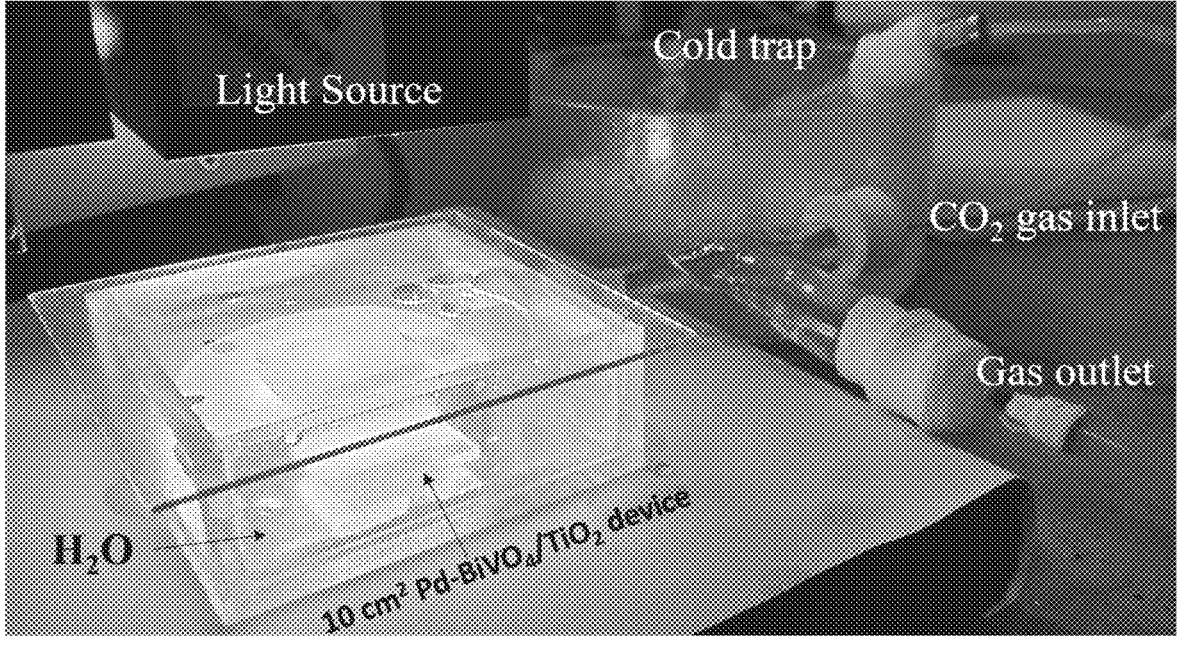
FIG. 8 represents continuous process experimental set up for large scale device. This device can accommodate device sizes up to 100 $cm^2$.
Figure 8:
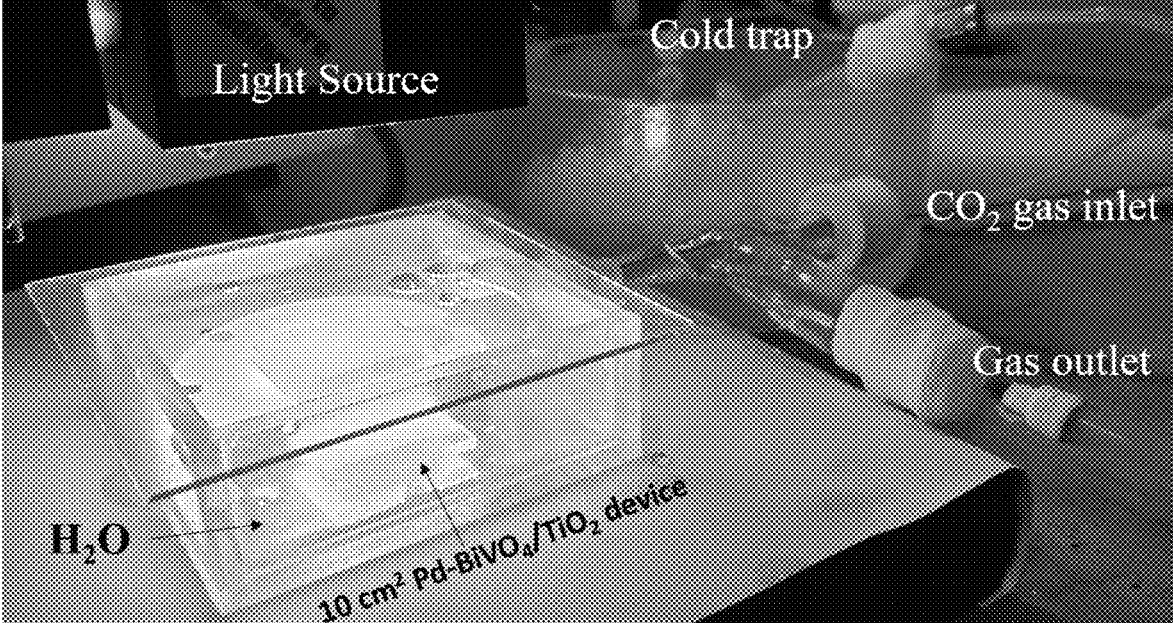

To maximize the conversion efficiency for photocatalytic co-conversion of $CO_2$ and water to value added products, a continuous process was adopted, in which $CO_2$ gas was continuously bubbled in to the solution throughout the reaction. A continuous flow of $CO_2$ has been carried out with Pd—BiVO$_4$/TiO$_2$ photocatalyst device in a specially designed reactor (shown in FIG. 8) in the presence of one sun condition as well as direct sunlight. Products vapour escaped into the gas phase was also collected outside of the reactor in a condenser or a trap kept in ice-bath and analyzed. Products in the liquid was also analyzed by HPLC, as in batch process. Both values are added to get the total products formation. Results obtained are given in Table 4 and compared with that of results obtained from batch process.

TABLE 4

CO₂ conversion and products selectivity and yield observed as a function
of irradiation time with 1 cm² size photoanode in continuous and
batch process under one sun condition as well as direct sunlight.

| Time/ | One sun Condition (μmol/cm²) | | | | Direct Sunlight (μmol/cm²) | | | |
| | Batch Mode | | Continuous mode | | Batch Mode | | Continuous mode | |
| h | CH₃OH | HCHO | CH₃OH | HCHO | CH₃OH | HCHO | CH₃OH | HCHO |
|---|---|---|---|---|---|---|---|---|
| 1 | 29 | 105 | 68 | 214 | 58 | 165 | 88 | 246 |
| 3 | 114 | 211 | 206 | 279 | 174 | 271 | 289 | 298 |
| 5 | 242 | 335 | 303 | 381 | 281 | 358 | 355 | 431 |

Figure 6:
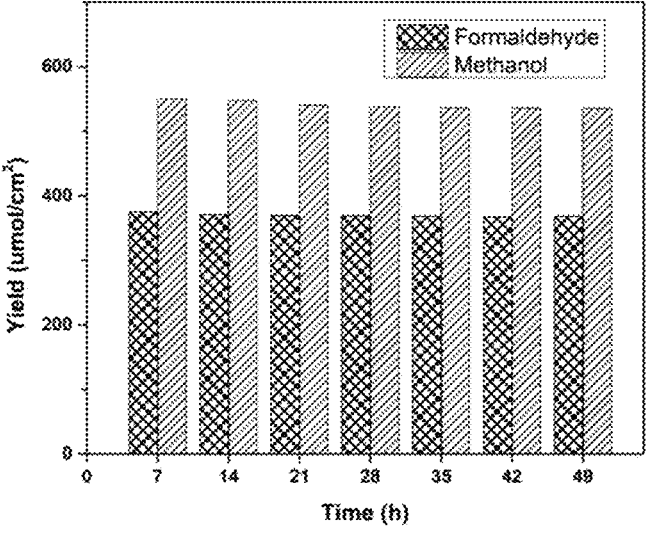
FIG. 6 represents stability study for the co-conversion of water and $CO_2$ in the presence of photocatalyst device made of the Pd—$BiVO_4$/$TiO_2$ under direct sunlight. This experiment was carried out for 7 h every day (anytime between 9 am and 5 pm) in March-April 2021.
Figure 7:
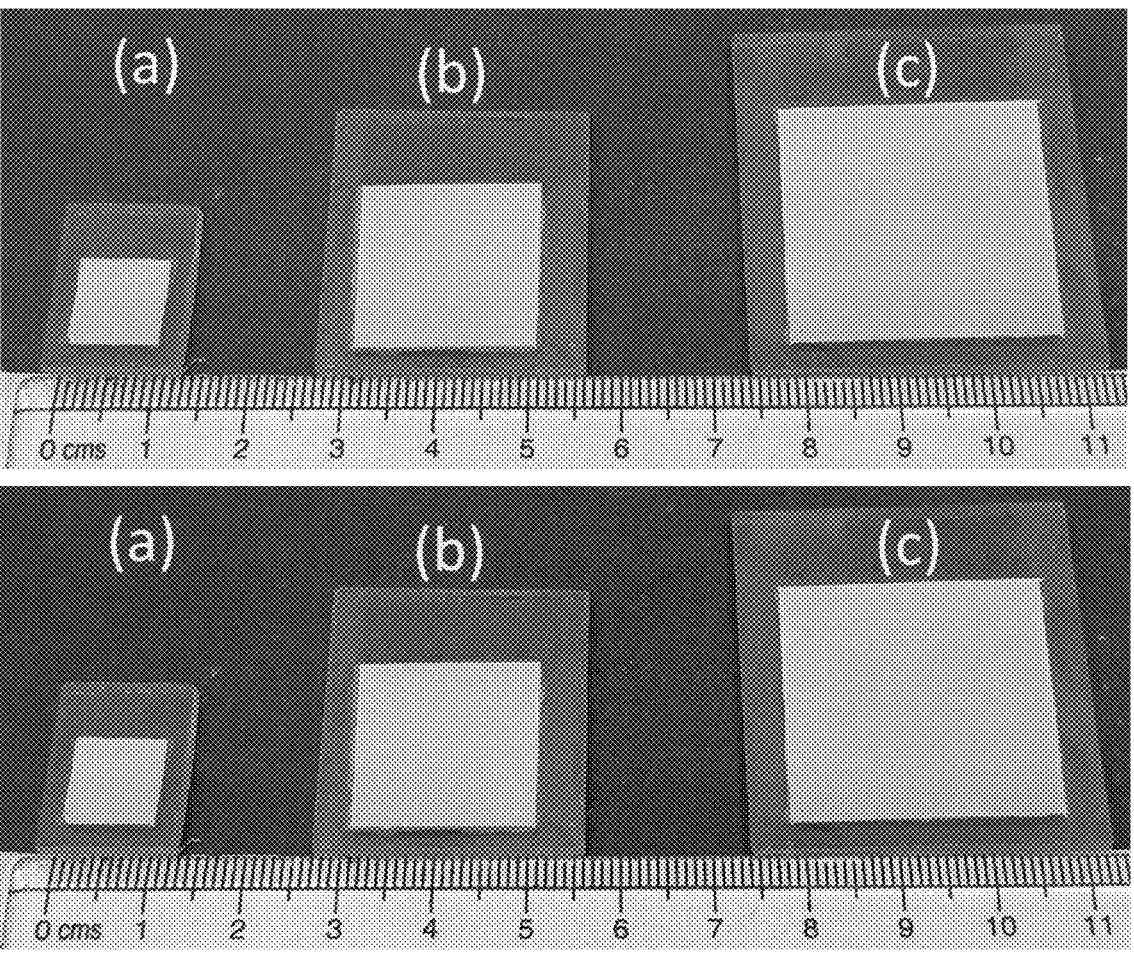
FIG. 7 represents digital photograph for the device fabricated from 1 to 9 $cm^2$ of photoanode $BiVO_4$/$TiO_2$

It is clear from Table 4 that continuous process enhances the $CO_2$ conversion rate than the batch process, irrespective of one sun or direct sunlight conditions; it is also to be noted that direct sunlight enhances the rate than the batch process. Light flux from sunlight plays an important role to enhance the reaction rate. Another important observation is the selectivity trend of the products remains the same, irrespective of batch or continuous process. While the rate of $CO_2$ conversion (and products formation) increases to 2.5 times initially (1 h) with continuous process (337 μmol) in sunlight from batch process (134 μmol) under one sun condition after 5 h of reaction this trend shows 1.4 time increase in yield from batch to continuous mode. By simply running reaction for longer hours in direct sunlight, preferably for 7 h anytime between 9 am to 5 pm, 1 cm² device shows yield for methanol 547 μmol (59% selectivity) and for formaldehyde 370 μmol (41% selectivity). Furthermore, stability of device is evaluated in presence of direct sunlight for 50 h and the result is shown in FIG. 6. The device shows constant product yield even at 50 h of reaction indicated the stability of the device for sustainable photocatalytic co-conversion of $CO_2$ and water into value added products. More studies has been carried out by continuous process under direct sunlight with 4 cm²(2 cm×2 cm) and 9 cm² (3 cm×3 cm) photoanode device (FIG. 7), and product yield observed with them are shown in Table 5.

with that of the standard samples. Calibration curve was obtained to correlate the concentration of methanol and formaldehyde to the HPLC peak area. HPLC, equipped with RI detector (at 40° C.) and H⁺ Aminex column (305 mm×7.8 mm) fitted with a guard column in series. Mobile phase used was 0.03 M $H_2SO_4$ at a flow rate of 0.6 mL min⁻¹ while maintaining the column temperature at 60° C. as well as gaseous product were analyzed by using Gas chromatography equipped with TCD detector and Carbosieve S II column, carrier gas is Helium and column temperature is 100° C. But in current experiments no formation of gaseous reduction product from the reaction such as $CH_4$ or CO. Only oxidized product i.e. oxygen is analyzed using Gas Chromatography.

A series of control experiments are carried out in order to confirm the origin of photoactivity of $BiVO_4/TiO_2$ photoanode. $CO_2$ and $H_2O$ filled reactor with photocatalyst film of Pd—$BiVO_4/TiO_2$ kept in dark for overnight and no reaction product were detected in this case. When only $BiVO_4$ thin film is placed under irradiation with $CO_2$ and $H_2O$, no activity observed. Finally, if Pd/$TiO_2$ was irradiated no conversion products were detected as in this case water splitting is more dominant reaction as compared to $CO_2$ reduction reaction.

It is observed much better formation rate for methanol in saturated $CO_2$ condition in pure water without using any

TABLE 5

CO₂ conversion and products selectivity and yield observed as a function of
irradiation time with 4 and 9 cm² photoanodes integrated with Pd co-catalyst.

| Time/ | 4 cm² Device (μmol) | | | | 9 cm² Device (μmol) | | | |
| h | CH₃OH | Selectivity | HCHO | Selectivity | CH₃OH | Selectivity | HCHO | Selectivity |
|---|---|---|---|---|---|---|---|---|
| 1 | 241 | 26% | 685 | 74% | 533 | 25% | 1525 | 75% |
| 3 | 804 | 43% | 1076 | 57% | 1765 | 41% | 2447 | 59% |
| 5 | 968 | 45% | 1179 | 55% | 2163 | 45% | 2645 | 55% |
| 7 | 1523 | 59% | 1045 | 41% | 3436 | 59% | 2387 | 41% |

4 cm² photoanode device shows ~3 times higher value of products yield, while 9 cm² size device shows ~6 times higher value of product yield compared to 1 cm² device under direct sunlight. Interestingly both devices exhibit same selectivity trends for the products and it is worth highlighting.

High performance liquid chromatography (HPLC, Agilent technologies, modal 1250 infinity) was used to analyze the liquid samples for the identification of the reduction product such as methanol formaldehyde etc. The formation of products was confirmed by matching experimental data sacrificial agent, which is 48±5 μmol/h/mg with 48% selectivity and one more value added product, HCHO observed with methanol having formation rate 67±5 μmol/h/mg in saturated $CO_2$ solution. In total Pd—$BiVO_4$ QDs in $TiO_2$ device able to reduce 115±5 μmol/h/mg $CO_2$ to value added products.

Different catalyst structure of one photocatalyst is another key reason for obtaining different. hence as compared to lamellar $BiVO_4$, quantum dots $BiVO_4$ plays vital role to enhance $CO_2$ reduction activity by creating heterojunctions in pore of $TiO_2$ throughout the film leads to effective separation of electron-hole pair and well dispersion of electron towards co-crystal, ultimately lead to greater yield and higher rate of formation than observed in lamellar $BiVO_4$.

EXAMPLES

Following examples are given by way of illustration therefore should not be construed to limit the scope of the invention.

Example 1: Photocatalyst Thin Film Preparation

Substrate chosen in this method was FTO plates. Initially FTO plates were properly cleaned with isopropyl alcohol followed by $TiCl_3$ treatment on conductive side of FTO. $TiO_2$ paste was coated by doctor blade method to 1 cm² area of plate and dried at 60° C. for 2 hr and then calcined at 450° C. for 30 min. Detailed procedure for $TiO_2$ paste is as follows: 1 g of $TiO_2$ powder (Degussa P25) was stirred for 10 min with 33 ml ethanol and 0.33 ml glacial acetic acid and then sonicated for 10 min. 0.5 g ethyl cellulose was added to the above mixture with 10 min stirring and 10 min sonication. Finally 3 ml of terpineol was added to the mixture and kept for 30 min stirring and sonication. After this solvent was evaporated to obtain a uniform thick paste by using rota vapour. This titania paste was coated on FTO plate uniformly and the thickness of such films are in the range of 8-14 μm.

Herein to make a photocatalysis device to work with high efficiency in the maximum range of solar radiation hetero-junction has been created by assembling the quantum dots in the pores of $TiO_2$; more particularly semiconductor used for creating heterojunction in this case is $BiVO_4$, by SILAR method. More details are as follows:

Bi-ion containing solution was prepared by mixing 25 mMBi(NO_3)_3 in the mixture of acetic acid and water, with a ratio 1:19, at 25° C. Similarly, 25 mM $NH_4VO_3$ solution was prepared by dissolving required amount of $NH_4VO_3$ in water at 75° C. Both solutions were used in SILAR method to deposit $BiVO_3$ QDs in the porous structure of titania film. Pre-coated $TiO_2$ film on FTO was immersed in Bi-bath for 20 seconds followed by immersion in V-bath for another 20 seconds. This was one SILAR cycle. Amount/content of QD in the titania film was gradually increased as the number of SILAR cycle subjected was increased; particularly, 10 SILAR cycles were applied on $TiO_2$ film for the maximum activity of the device. Film was rinsed with deionized water and dried in air after each cycle, after 10 SILAR cycles, film was annealed in air at 450° C. for 2 h to form uniform $BiVO_4$ QDs in the pores of $TiO_2$ Thus, one part of device resulted in $BiVO_4$/$TiO_2$ photoanode.

Example 2: Photocatalyst Thin Film Preparation CdS/TiO_2

$TiO_2$ film is coated on FTO plate for 1 cm² size with doctor blade method as explained in example 1. To make the device active in solar radiation, CdS is used as quantum dot by SILAR method. Details are as follows: Pre-coated $TiO_2$ film was first immersed in aqueous solution of cadmium precursor (i.e. 0.1 M Cd (NO_3)_2) for 1 min at 25° C. then washed with deionized water followed by immersion in sulphide precursor with 0.1 M $Na_2S$ solution at 25° C. for 1 min. This is known as one SILAR cycle of CdS. Five such SILAR cycles of CdS was carried out on $TiO_2$ film. To avoid photo-corrosion, 2 SILAR cycles of ZnS was carried out using 0.1 M Zn(CH_3CHOO)_2 and 0.1 M $Na_2S$ solution for 1 min each. ZnS is used as a passivating layer. Finally, the film is dried at 60° C. in oven. This is another example of fabricated photoanode devices labeled as CdS/TiO_2 photo-anode.

Example 3: Synthesis of Co-Catalyst: Pd Nanoparticles

The synthesis of the Pd nanocubes(Pd_{NC}) with dominant (100) facets is synthesized as follows. In 8 mL of water, 105 mg of PVP (poly vinyl pyrrolidone), 60 mg of ascorbic acid, and 300 mg of KCl were added in 25 mL 3-neck round bottom flask (RBF), and kept at 90° C. under constant stirring. After five minutes, 3 ml of water containing 57 mg of $K_2PdCl_4$ was added to the above solution and kept at the same temperature (90° C.) for 3 h under constant stirring. After 3 h, the obtained brown-black colored nanoparticle solution was cooled to 25° C. and collected in centrifuge bottles. The cleaning of the nanoparticles was carried out by centrifuging the solution one time with excess amount of acetone and three times with ethanol/hexane mixture (1:5 ratios) at 10,000 rpm for 10 minutes. The final precipitate was dispersed in water for further cleaning.

Example 4: Synthesis of Co-Catalyst-NiCu Alloy Nanoparticles

NiCu nanoparticles was synthesized by solvothermal techniques with the help of oleylamine as capping as well as reducing agent. The detailed synthesis procedure of NiCu nanoparticles is as follows: In a 100 ml three neck round bottom flask, 25 ml of oleylamine was taken and kept at 120° C. for 10 min to remove any trace amount of water from oleylamine. 2:1 mole ratio of nickel and copper pre-cursors, nickel (II) nitrate hexahydrate and copper (II) acetate monohydrate, was added to this preheated oleylam-ine. The reaction mixture was gradually increased to 220° C. and kept at 1 hr under magnetic stirring. After 1 hr, colour of the solution changed from green to black, indicating the formation of NiCu alloy nanoparticles. The resultant black solution was cooled to 25° C. and then the nanoparticles formed were separated by centrifugation. Followed by washing with ethanol and centrifuged; this procedure was repeated three times and finally nanoparticles are collected in ethanol solvent.

Example 5: Synthesis of Co-Catalyst: Half Mono-layer Pt Covered on NiCu Alloy (0.5θ_{Pt}@NiCu)

Half monolayer of Pt covered on NiCu alloy was synthe-sized by a special method. As explained in Example 4, NiCu alloy nanoparticles were prepared initially. NiCu alloy was treated with $NaBH_4$ in ratio 1:4 with ethanol under stirring for 30 min in round bottom flask (RBF). This is followed by refluxing the solution at 80° C. for 1 h. Then it was centrifuged, washed with ethanol and named as NiCu@H⁻ as NiCu alloy surface is covered by hydride ions. NiCu@H⁻ is treated with $K_2PtC_{14}$ in 8:1 ratio with ethanol in RBF and sonicated for 30 min and then refluxed at 74° C. for 12 h. Finally it was centrifuged, washed with ethanol to get 0.5θ_{Pt}@NiCu.

Example 6: Synthesis of Co-Catalyst-NiFe Nanoparticles

NiFe nanoparticles was synthesized by hydrothermal technique. The detailed synthesis procedure of NiFe nanoparticles is as follows: for the preparation of 1:3 NiFe nanoparticle 0.025 M of nickel nitrate and 0.075 M iron-nitrate precursor was taken and dissolved in 10 ml distilled water. 10 ml of 1 M NaOH solution was added under stirring for 10 min for formation of alkaline solution. 5 ml of hydrazine solution was added to the solution to reduce metal ions; also 0.01 M sodium dodecyl sulfate was added as surfactant and kept for stirring for 2 h at 30° C. Solution was transferred to teflon lined autoclave and was kept in oven at heated at 140° C. for 6 h. After cooling to room temperature, solution was washed with de-ionized water and ethanol, dried in oven at 60° C. for 2 h. This co-catalyst is named as NiFe.

Example 7: Synthesis of Half Monolayer Pt Covered on NiFe ($0.5\theta_{Pt}$@NiFe) Co-Catalyst First NiFe was synthesized by solvothermal method, as described in example 6. NiFe alloy was treated with $NaBH_4$ in the ratio of 1:4 with ethanol under stirring for 30 min in a RBF followed by refluxing at 80° C. for 1 h. Then it was centrifuged and washed with ethanol and it is named as NiFe@H⁻ as NiFe alloy surface is covered by hydride ions. NiFe@H⁻ was treated with $K_2PtCl_4$ in 8:1 ratio in ethanol in a RBF. This solution was sonicated for 30 min and then refluxed at 74° C. for 12 h. Then it was centrifuged, and washed with ethanol and dried. This is known as $0.5\theta_{Pt}$@NiFe.

Example 8: Synthesis of Half Monolayer Pt Covered on Pd Nanoparticles ($0.5\theta_{Pt}$@Pd)

As explained in Example 3, Pd nanoparticles ($Pd_{NC}$) was prepared first. $Pd_{NC}$ NP was treated with $NaBH_4$ in a ratio of 1:4 with ethanol under stirring 30 min in a RBF, followed by refluxing at 80° C. for 1 h. Then it was centrifuged, washed with ethanol and named as Pd@H⁻. In 25 mL RBF, to the solution (10 mL) of Pd@H⁻ nanoparticles, the desired amount of $K_2PtCl_4$ dissolved in 5 mL of water (for half-a-monolayer of Pt over Pd) was added and kept for sonication for 30 min. and thereafter kept at 70° C. under constant stirring for 12 h. The final solution was cleaned at 30° C. with water. The final precipitate was collected and dried for 12 h at 60° C. for applications. This catalyst is indicated as $0.5\theta_{Pt}$@Pd.

Example 9: Photocatalytic $CO_2$ Reduction (Batch Process)

1 cm² area thin film photocatalyst device was prepared with 1 mg of Pd—$BiVO_4$/$TiO_2$ and integrated with Pd-co-catalyst. This photochemical device was kept in 30 ml of deionized water at pH=7, where water would act as in-situ hydrogen source in 50 ml of quartz reactor and sealed using septum. The reaction mixture was thoroughly saturated with $CO_2$ using 99.9% $CO_2$ gas for about 40 min. pH of the solution was measured to be 6.2 indicating the acidic nature of the solution due to $CO_2$ dissolution. To dissolve the maximum amount of $CO_2$ in water, the reaction flask was placed in ice bath at time of saturation. The reaction flask was illuminated under one sun condition in static condition for at least 5 hrs. To analyses product aqueous as well as gas phase sample were withdrawn at steady interval of time using tightly closed syringe. No gas phase product was observed; while liquid products are analyzed by HPLC method.

Example 10: Photocatalytic $CO_2$ Reduction (Batch Process): NiCu—$BiVO_4$/$TiO_2$ Thin Film As stated in example 5, $BiVO_4$/$TiO_2$ thin film photocatalyst device was prepared by doctor blade followed by SILAR method. Instead of Pd, NiCu alloy cocatalyst was integrated. This device was subjected to the co-conversion of $CO_2$ with water, as stated in example 9. It is observed that this device is selective toward reduction of $CO_2$ and shows marginally lower activity compared to its Pd-counterpart.

Example 11: Photocatalytic $CO_2$ Reduction (Batch Process): Pd—CdS/$TiO_2$ Thin Film As described in example 2 Cds QD decorated $TiO_2$ film was prepared as photoanode and integrated with Pd as cocatalyst. This device Pd—CdS/$TiO_2$ was evaluated for $CO_2$ reduction activity as described in example 9. This device was found to be significantly effective for water splitting also.

Example 12: Photocatalytic $CO_2$ Reduction (Continuous Process)

A continuous flow of $CO_2$ has been carried out with Pd—$BiVO_4$/$TiO_2$ photocatalyst device in a specially designed reactor (FIG. 8) in the presence of direct sunlight. Products formed in the gas phase was collected outside of the reactor in a condenser or a trap kept at ice-bath and analyzed. Products in the liquid was also analyzed as in example 9 by HPLC method. Products present in the aqueous solution was analyzed and added to the value obtained from condensed products to get the total products formation. Other reaction conditions were same as explained in first method. Although selectivity remains same as shown in Table 1, the yield of product formation was observed to increase to 2.5-3 times. This indicates the high rate of reaction in direct sunlight.

Example 13: Photocatalytic $CO_2$ Reduction (Continuous Process): NiCu—$BiVO_4$/$TiO_2$ Thin Film As described in example 1 $BiVO_4$ QD decorated $TiO_2$ film was prepared as photoanode and integrated with NiCu as cocatalyst (as described in example 4). This device NiCu—$BiVO_4$/$TiO_2$ was evaluated for $CO_2$ reduction activity as described in example 12. It is observed that this device is selective toward reduction of $CO_2$ and shows marginally lower activity compared to its Pd-counterpart.

Example 14: Photocatalytic $CO_2$ Reduction (Continuous Process): $0.5\theta_{Pt}$@NiCu—$BiVO_4$/$TiO_2$ Thin Film As described in example 1, $BiVO_4$ QD decorated $TiO_2$ film was prepared as photoanode and integrated with $0.5\theta_{Pt}$@NiCu as cocatalyst. This device was evaluated for $CO_2$ reduction activity as described in example 12. Here noticeable amount of $CH_4$ as reduction product is also observed with clear indication of bubbles from device.

Example 15: Photocatalytic $CO_2$ Reduction (Continuous Process): NiFe—$BiVO_4$/$TiO_2$ Thin Film As described in example 1 $BiVO_4$ QD decorated $TiO_2$ film was prepared as photoanode and integrated with $0.5\theta_{Pt}$@NiFe as cocatalyst. This device NiFe—BiVO$_4$/TiO$_2$ was evaluated for CO$_2$ reduction activity as described in example 12. NiFe—BiVO$_4$/TiO$_2$ device is found to be selective exclusively towards methanol as the CO$_2$ reduction product.

Example 16: Photocatalytic CO$_2$ Reduction (Continuous Process): $0.5\theta_{Pt}$@NiFe—BiVO$_4$/TiO$_2$ Thin Film As described in example 1 BiVO$_4$ QD decorated TiO$_2$ film was prepared as photoanode and integrated with $0.5\theta_{Pt}$@NiFe as co-catalyst. This device $0.5\theta_{Pt}$@NiFe—BiVO$_4$/TiO$_2$ was evaluated for CO$_2$ reduction activity as described in example 12. $0.5\theta_{Pt}$@NiFe—BiVO$_4$/TiO$_2$ shows more methanol formation as compared to example 15.

Example 17: Photocatalytic CO$_2$ Reduction (Continuous Process): $0.5\theta_{Pt}$@Pd—BiVO$_4$/TiO$_2$ Thin Film As described in example 1 BiVO$_4$ QD decorated TiO$_2$ film was prepared as photoanode and integrated with $0.5\theta_{Pt}$@Pd as cocatalyst. This device was evaluated for CO$_2$ reduction activity as described in example 12. With this device both formaldehyde and methanol is observed as CO$_2$ reduction products, and it is similar to Pd-counterparts. However, more methanol is observed with this device, than that of only Pd-counterpart device.

Advantages of the Invention

Simple and efficient method for photocatalytic co-conversion of a mixture of carbon dioxide and water to value added chemicals in direct sunlight with economically viable photocatalyst device Dual-functional photocatalyst (water reduction as well as CO$_2$ reduction) by assembling precursors of light-absorbing photocatalyst quantum dots in the mesopores of wide band gap semiconductors is provided.

Co-conversion of carbon dioxide and water to value added chemicals in direct sunlight is demonstrated to be a continuous process.

Significant increase in process and catalyst temperature due to solar irradiation enhances the rate of reaction at no cost.

Thin film photocatalyst device size is scaled up to 9 cm$^2$ without loss of activity and can be easily scaled up further, and hence the problems associated with powder catalyst are not present.

Entire photocatalytic co-conversion can be carried out with different light sources, such as direct sunlight, standard laboratory light sources, UV, UV+Visible light sources.

Product selectivity and conversion efficiency can be tuned by employing different co-catalyst.

The present work has directly demonstrated the reduction of CO$_2$ to formaldehyde and methanol.

The present proposed device in thin film form where light absorption happens throughout the entire thickness of device and better contact which enable charge diffusion and charge utilization over large scale of device, helps to improve high efficiency.

Stable activity is demonstrated for at least 50 h while maintaining product yield and selectivity.

It is neither BiVO$_4$ nor TiO$_2$ alone can do the CO$_2$ reduction along with water splitting leading to formaldehyde and methanol. Indeed, it is a unique combination of BiVO$_4$ QDs in the pores of titania leading to effective light absorption by BiVO$_4$ followed by charge separation leading to the highest sustainable activity, as well as scalability.

With no pH adjustment, sustainable CO$_2$ conversion activity to value added products has been demonstrated in direct sunlight in batch and continuous modes of reaction.

Much higher activity observed with the present BiVO$_4$ QDs assembled in the titania pores with sequential reduction of CO$_2$ to formaldehyde to methanol is highly unique.

We claim:

1. A dual functional photocatalytic device comprising:
   a photoanode including a wide band gap semiconductor thin film having mesopores therein and nanostructures of a visible-light absorbing semiconductor assembled in the mesopores of the wide band gap semiconductor thin film; and
   a co-catalyst integrated with the photoanode;
   wherein the visible-light absorbing semiconductor comprises at least one of: an earth abundant 3d or 4d transition metal, a metal oxide of an earth abundant 3d or 4d transition metal, CdS, PbS, and combinations thereof;
   wherein the wide band gap semiconductor from comprises TiO$_2$ or ZnO; and
   wherein the co-catalyst comprises at least one of: an earth abundant 3d or 4d transition metal, a metal oxide of an earth abundant 3d or 4d transition metal, an alloy comprising an earth abundant 3d or 4d transition metal, palladium (Pd), platinum (Pt), gold (Au), silver (Ng), silicon (Si), and combinations thereof.

2. The device as claimed in claim 1, wherein said visible-light absorbing semiconductor is selected from the group consisting of BiVO$_4$, CdS and PbS.

3. The device as claimed in claim 1, wherein the nanostructures of said visible-light absorbing semiconductor comprise quantum dots (QDs) of the visible-light absorbing semiconductor assembled in the mesopores of the wide band gap semiconductor thin film.

4. The device as claimed in claim 1, wherein said co-catalyst is selected from the group consisting of palladium (Pd), platinum (Pt), gold (Au), silver (Ag), nickel (Ni), cobalt (Co), cuprous oxide (Cu$_2$O), a NiCu alloy, titanium (Ti), silicon (Si), zinc (Zn), nickel oxide, manganese oxide, one or more iron oxides, NiFe, $0.5\theta_{Pt}$@NiFe, $0.5\theta_{Pt}$@NiCu, $0.5\theta_{Pt}$@Pd, a NiFe alloy, and a Pt-coated NiCu alloy.

5. The device as claimed in claim 1, wherein said device shows stable activity for 50 h while maintaining product yield and selectivity.

6. A process for the photocatalytic co-conversion of a mixture of CO$_2$ and water to one or more value added products in batch mode comprising the step of:
   injecting CO$_2$ into water to maximum saturation level and placing a photocatalytic device of claim 1 in a quartz reactor under light source at a temperature in the range of 1 to 60° C.;
   wherein said light source comprises at least one of UV+Visible light, visible light, and direct sunlight.

7. A process for the photocatalytic co-conversion of a mixture of CO$_2$ and water to one or more value added products in continuous mode comprising the step of:
   i) continuously flowing CO$_2$ through water with photocatalytic device of claim 1 in a quartz reactor under light source at a temperature in the range of from 1° C. to 60° C.;
   wherein said light source comprises at least one of UV+Visible light, visible light, and direct sunlight.

8. The process as claimed in claim 6, wherein the one or more value added products comprises one or both of methanol and formaldehyde.

9. The process as claimed in claim 6, wherein conversion efficiency of said carbon dioxide to the one or more value added products is from 35% to 55%.

10. The process as claimed in claim 6, wherein said process is tunable to generate desired value-added products comprising methanol and formaldehyde.

11. The process as claimed in claim 7, wherein the one or more value added products comprises one or both of methanol and formaldehyde.

12. The process as claimed in claim 7, wherein conversion efficiency of said carbon dioxide to the one or more value added products is from 35% to 55%.

13. The process as claimed in claim 7, wherein said process is tunable to generate desired value-added products comprising methanol and formaldehyde.

14. The device as claimed in claim 1, wherein the nanostructures of the visible-light absorbing semiconductor are assembled by introducing one or more precursor ions into the mesopores of the wide band gap semiconductor thin film and converting the one or more precursor ions to the visible-light absorbing semiconductor to form the nanostructures within the mesopores.

15. The device as claimed in claim 14, wherein the one or more precursor ions are introduced uniformly across the entire thickness of the wide band gap semiconductor thin film.

16. The device as claimed in claim 1, wherein the nanostructures of the visible-light absorbing semiconductor are distributed in the mesopores across the entire thickness of the wide band gap semiconductor thin film.

17. The device as claimed in claim 1, wherein the nanostructures of the visible-light absorbing semiconductor form heterojunctions with the wide band gap semiconductor within the mesopores of the wide band gap semiconductor thin film.

18. The device as claimed in claim 1, further comprising a planar support structure configured to support the photoanode and the co-catalyst.

19. The device as claimed in claim 1, wherein the co-catalyst are in the form of nanoparticles integrated with the photoanode.

* * * * *